United States Patent [19]

Herrera-Estrella et al.

[11] Patent Number: 5,922,603

[45] Date of Patent: Jul. 13, 1999

[54] **METHOD FOR OBTAINING STRAINS OF *TRICHODERMA* SPECIES**

[76] Inventors: Alfredo H. Herrera-Estrella, Rincon Del Romance No. 124, Fracc. Las Plazas, C.P. 36620, Irapuato, Guanajuato, Mexico; Alberto Flores-Martinez, Rio San Francisco No. 1363, Fracc. La Pradera, C.P. 36630, Irapuato, Guanajuato, Mexico; Ilan Chet, Saikun-Ezrahi, Nes Ziona, 74046, Israel

[21] Appl. No.: 08/849,345

[22] PCT Filed: Dec. 8, 1995

[86] PCT No.: PCT/MX95/00009

§ 371 Date: Jul. 25, 1997

§ 102(e) Date: Jul. 25, 1997

[87] PCT Pub. No.: WO96/18722

PCT Pub. Date: Jun. 20, 1996

[30] Foreign Application Priority Data

Dec. 8, 1994 [MX] Mexico ..................................... 949542

[51] Int. Cl.⁶ .............................. C12N 1/15; C12N 15/31; C12N 15/80; A01N 63/04

[52] U.S. Cl. .......................... 435/480; 435/471; 435/484; 435/254.6; 424/93.2

[58] Field of Search .............................. 435/172.3, 254.6, 435/484, 471, 480; 424/93.2

[56] References Cited

U.S. PATENT DOCUMENTS 5,288,624 2/1994 Nielsen ..................................... 435/128

5,389,609 2/1995 Woloshuk et al. ........................ 514/12

OTHER PUBLICATIONS

Sivan et al., J. Gen. Microb. 135:675–682 (1989).

Ulhoa et al., Curr. Genet. 21:23–26 (1992).

Sánchez–Torres et al., Appl. Microbiol. Biotechnol. 41:440–446 (1994).

Geremia et al., Molecular Microbiology 8(3):603–613 (1993).

Goldman et al., Curr. Genet. 17:169–174 (1990).

Lorito et al., Curr. Genet. 24:349–356 (1993).

*Primary Examiner*—Johnny F. Railey, II
*Attorney, Agent, or Firm*—Rothwell, Figg, Ernst & Kurz, P.C.

[57] ABSTRACT

Strains of Trichoderma spp. that are improved in their capacity as biological control agents for phytopathogenic fungi and nematodes are obtained that are able to overproduce a proteinase, with the aid of a transformation method which involves introducing the gene prb1 of Trichoderma that codes for the proteinase PrB1 under the control of adequate means of regulating expression, producing multiple copies in a stable manner; this ensures that the control achieved of the disease that is caused by pathogenic fungi or nematodes is better in the transgenic strain than in the uncultivated strain that is used as a receptor of the genetic information.

28 Claims, 6 Drawing Sheets

```
            10         20         30         40         50
      1234567890 1234567890 1234567890 1234567890 1234567890
      AATTCAACTT TATTCACAAC GTTTTTTGTC GACTTCTAGC TTAGAGCTAC   50
      TGTATTTGTT AATATTTGTT CAGTGGCTGC AAAATTACAT CCCAAGCCAT  100
      TCGCTGCTAC ATAAATCATG GGCTATAAGA ACCAACACAA TTCTTATTAG  150
      ACGTAGTAAT ACCTAGGTAC CTTACTTGGC AATACGCCTT ACGATGAGTT  200
      CAATGTGGGG ATTTTATGAG CAAAGATTGA AAATATTGAT GCAATTACTT  250
      TTTCGGGTAT TGGTTTCCAC TTGCGGAAGA CTGTCTAGTA GTACATCTTT  300
      CACGATCAAA AATATCACAT GTCGTTTACC ATCTCTTATC GCTCACAATC  350
      TTCAGCCGCC TTGTAGGAGC AGCATGGATA ATAATCCGAG ATCCCAGCGC  400
      TCTATAATAG CGGATTCCCC ATAACGTACA ATCCGTAATA TTGAAAACTT  450
      TGGTTACTCA GCGAGGTGGC AGAATCACCT TCCCATTCGG GCAATATAAA  500
      AAGTTCCGCT ATTCGGCCAC CCCTCCTTCT TAAATCTTGA TAAGGCGCCG  550
      GCTATGATTG CGCTATTAGA GCCTTGCCGT GCGTTCTATT CAAAGGTTCC  600
      TTGATTCTCG GACATGATAA CTTAAAAAGC AGGTGCACAG CTATTGGCGC  650
      GATTTTAGTC CGCACGGCAT TCGGCATTTT TACCTGTGAT ACAAACAACC  700
      CATCGAGAGT TCGATTTTAA GCGTAAATAT TAGCGAATCT TAGTCTATAG  750
      GCGTCAAATA ACCTTAAATG AATCTTAAAT TGTATGGGTT CGCTATTTGT  800
      ATTATTTGTC CGGTAGTGAT GAGGAGATTG GAGACAGCGC ATTTGGAGTG  850
      GGAATGATGA AAAGCAAGAC GGCTATTCAT AGAAATAGAC CATGTATTAA  900
      ACCATCTTCA TCGATATCCA AGTTGATGCC TTGGAGATAC TGCTTCTTCA  950
      TCATGCTTCT TTCCGCATTC AAACTAGCTG CCAAGATCTG GGCACCGTGG 1000
      CTGCCGTAAC ACAAACCTAT AGTCTTGGTG TGATCTATTC GTTCTAGTTC 1050
      TTTTTAGGCA GCTTGGATAT CTATACTCAG CGGCTTGGCA AGCAATTACA 1100
      ATGGAGTGAT TCTGGCAGAC GTGATGGAGG CTTCAGATAG CGAAATCGAG 1150
      CATATCATCC GCAGTGACAA TGAAAACTAT TTAAGTTGGC TGTATTCGCA 1200
      AGAATATCTG GTAAGTTGGA ACAGCCATCG ACTTCCTATC TTTTCTCCTC 1250
      CACTATACAA AGCACATCAC AGCCATGACC AGCATTCGTC GTCTCGCTCT 1300
      CTATCTTGGA GCTTTGCTCC CGGCTGTCCT CGCTGCTCCT GCAGCTCTTC 1350
      ACAAGAAGCC TGAACCCGTA CCCAACAAGT TCATCGTCAC TCTTAAAGAG 1400
      GGTGCTTCTA TTGATACCGA CTCTCATCTC GCCTGGGTAA CGGACATCCA 1450
      CACCCGTTCG TTGACCAAGC GTAGCACTGC TGGTGTTGAA AAGACTTATA 1500
      ACATTCATAC TTGGAATGCT TATCCGGGCG AGTTTGACGA GGAGACAATT 1550
      GAGCAGATCA AGTCCAACCC CGATGTACGT CTCCGCTGTA TTGTGAAGAT 1600
      AAAAGAACAA AAAGAAGCTA ATCACACTAT AGGTTGCGTC TGTTGAGCCA 1650
      GACTACATCA TGCATCTGTC GGACATTGTT GAACACAAGC GTGCTCTGAC 1700
      CACACAATCT GGTGCTCCTT GGGGTCTCGG CACTGTGTCC CATCGCACAT 1750
      CTGGATCCAC AAGCTACATT TATGATAGCT CAGCCGGCGC CGGCACCTTT 1800
      GCCTATGTGG TTGACTCTGG TATCAACACT TCTCATCAGC AATTCGGCGG 1850
      GCGTGCCAGC CTTGGCTACA ATGCTGCAGG AGGACAGCAT GTCGATACTC 1900
      TTGGCCATGG TACTCATGTT TCCGGAACAA TTGGTGGATC TACATACGGT 1950
      GTTGCTAAGC AGGTGAGCTA CCCTTTGTCG ACTTTTTGTT GTGAATACAT 2000
      GAATGCATTC AAGACTAACT CGGTACTGCT CATAGGCGAG CCTAATCTCT 2050
      GTCAAGGTCT TTGCTGGTGA AAGTGCTTCC ACCTCTGTTA TCCTTGACGG 2100
      CTATAACTGG GCTCTAAACG ACATCGTCTC GAAAAGCCGT GCTAGCAAGT 2150
      CTGCTATTAA CATGTCGCTT GGAGGACCTG CCTCATCTAC CTGGACGACC 2200
      GCCATTAACG CAGCCTTTAA CCAGGGCGTG CTTACCATTG TCGCCGCTGG 2250
      TAATGGCGAC TCTCTGGGAA ACCCCAGCC AGTCTCCGGC ACTTCTCCTG 2300
      CTAACGTTCC TAACGCCATA ACCGTTGCCG CATTGGACAT CAACTGGCGC 2350
      ACTGCTTCCT TCACCAACTA TGGTGCTGGC GTTGATGTTT TTGCCCCTGG 2400
      CGTCAACATT CTGTCGTCAT GGATTGGATC CAACACTCCT ACCAACACAA 2450
      TCAGCGGTAC TTCCATGGCT ACACCTCACG TTGTTGGCCT GGCCCTCTAT 2500
      CTTCAATCTC TCGAGGGTCT CACCTCTCCG ACCGCTGTCA CTAACCGAAT 2550
      TAAAGCTCTG GCTACATCTG GTCGTGTAAC CGGAAGCCTC AACGGCAGCC 2600
```

FIGURE 1

|  10         20         30         40         50     |      |
|------------|------------|------------|------------|------------|------|
| 1234567890 | 1234567890 | 1234567890 | 1234567890 | 1234567890 |      |
| CCAACGTTAT | CATCTTCAAC | GGAAACAGTT | CTTAAATCGT | TGATGGAGCG | 2650 |
| AAGGATGAAG | TGAAATGTTC | ATGGAAGGGC | AGCACAGCTG | TTGCTTGGCT | 2700 |
| TGCTTAGCTC | ATTTAAGAAG | CTAATCACCA | TGATGGAGTG | CGATGGGTAT | 2750 |
| ATAAGCTTCT | CACAGCGTTT | TCAACTTAGC | TAGATGACCC | TCTATAGATC | 2800 |
| GCTAAAACAA | AAAGATATGA | CAGATACCTG | TGCTTTAATG | TTTCCTGACA | 2850 |
| CTGTGTAGTT | CGTTCCAAAA | CGGCGAATCT | TCTAGTATTG | TAACTGTATG | 2900 |
| ACATATATGT | CCTATCAGGA | TTAGGATTAG | GATTCGGATT | CGGATTATTA | 2950 |
| TTGCTGAAAA | TTAGAATATA | ATGATTCCCT | TTTGATGGCT | GTACAGTCGG | 3000 |
| AGGGTTTTAT | TTCCCGCATA | TAAAGTTATA | AACGCTGTGC | ACTCACTAGT | 3050 |
| GGTTCAATTC | TACAAATCAC | TAAATTTCTG | CGTTTCAATG | TATAGGTAGT | 3100 |
| CAAGGGCATT | GCATATCATA | TGTAAATTTT | CATTTCAATT | TCGAAAGTAA | 3150 |
| CGCTAAAGCA | GCTCTCTATA | CTTTGAACTC | CATCCGCAAT | CTATAGTTCT | 3200 |
| AAGACGCGCT | GAGAATATGT | AGCTCGCAGA | CATGTATTTA | GTTGACAATC | 3250 |
| TTCAGGGTCT | CGCTGAGGGG | AAGCTTCTCA | GGGACGGTGG | TGCTGTGGGG | 3300 |
| GCCGGGCTCA | TCACCATAGT | TCAAGTGGGC | CTTCAGTGAG | TAGTCGGCGG | 3350 |
| GCACCTGGAG | GAACTTCTTG | ATCTCTGCCT | CAACAGGAGG | AATGGCTTGC | 3400 |
| AAGTGCTGGA | GGTTGGCACC | CAATCCTTCC | AGCTCAAGAG | CGGTCCAGAC | 3450 |
| GAGGAGCTGA | GCCATACCGG | TCGAGTGCTC | CGCAAATTGG | CCGAACATGT | 3500 |
| GTGCGCCCGA | CTTGTGTGTC | TCTCCTGCTG | CCTTGATGCT | GTCACCACTC | 3550 |
| TCCCAGAAAA | CAACCTGCCG | TTTCGTCAGT | ATGGAAAGAA | TGATTTATAT | 3600 |
| AAAATAGTCT | CATCAGAGAG | GAGTAATGCC | TACCGATCCA | TATGATGCCT | 3650 |
| GTGCGACTCA | AAGATACC   |            |            |            | 3668 |

METHOD FOR OBTAINING STRAINS OF *TRICHODERMA* SPECIES

This is a national stage application under 37 CFR §371 of PCT/MX95/00009, filed Dec. 8, 1995.

FIELD OF THE INVENTION

This invention relates to the production of transgenic cells and organisms for controlling phytopathogenic fungi and nematodes and, more particularly, to a method for obtaining strains of Trichoderma spp. that are improved in their capacity as biological control agents for soils.

BACKGROUND TO THE INVENTION

The production of transgenic cells and organisms is opening a very interesting field in genetic engineering; said field is making it possible to incorporate a large number of desirable characteristics into organisms that are directly or indirectly beneficial to man.

At the current state of the art, the methods that are used to control phytopathogenic fungi and nematodes involve the use of large amounts of chemicals, which make it possible to select strains that are resistant to them, making them unsuitable for use in the future, in addition to the fact that they remain in the soil for long periods of time and may prove toxic to both humans and to other species of animals and plants.

Because of this, the ecosystem may be irreversibly affected, which is always undesirable.

One alternative, which people have attempted to apply more widely, is to use agents that exist in nature and are the natural enemies of the phytopathogen(s) to be controlled. Many organisms that can be used in this way have been described in the state of the art. However, the use of said control agents has been limited, primarily because in the majority of the cases the level of control has not been comparable to that achieved with a very efficient chemical fungicide.

Among the most successful agents for biological control of phytopathogenic fungi are those belonging to the genus Trichoderma. These organisms have been favored because they are able to control a wide variety of phytopathogenic fungi that are of great importance to agriculture.

Despite the relative success with which these organisms have been employed, it still has not been possible to achieve the desired levels of disease control.

Various techniques have been used in attempts to obtain organisms of this genus that have improved efficiency as biological control agents; the improvement techniques utilized include that of mutagenesis of both the physical and the chemical types, and protoplast fusion.

Even though the production of strains that have been improved by these techniques has been described, one of the most serious problems that has been encountered is that in these cases some of the organism's desirable characteristics may be affected since it is not possible to direct the changes toward a single type of characteristic, at least as far as is now known in the prior art.

These techniques do not make it possible to modify these organisms selectively, nor do they guarantee that improved strains will be obtained.

A reliable and highly effective way of modifying these organisms without altering characteristics of theirs that are desirable, while still making it possible to do so in a controlled manner, is to introduce the desirable characteristic using the segment of genetic information that codes it in order to transform said organism.

The existing techniques do not make it possible to modify said organisms selectively, nor do they guarantee that improved strains will be obtained.

To date, the literature has given a detailed description of three methods of transforming the genus Trichoderma.

The first of these methods is based on forming protoplasts of this organism and subsequently treating them with polyethylene glycol (PEG) and calcium chloride (CaCl), in combination with thermal shock and in the presence of transformant DNA; this makes it possible to introduce said DNA into the cell being treated. Once inside the cell, the DNA is incorporated into the genome of the microorganism by a mechanism that is inherent in this organism itself (Herrera-Estrella et al., 1990, "High efficiency transformation system for the biocontrol agent Trichoderma spp.", Molecular Microbiology, 4:839–843).

The second method is based on using cells that are treated with a mixture of enzymes that are able to weaken or remove their cell walls; these cells are subsequently subjected for a brief period to an electric current that is generated with high voltage; this causes the transient formation of pores in the membranes of the cells being treated. If the cells are subjected to this electric shock in the presence of DNA, the DNA is introduced into the cell via the pores and is incorporated into the microorganism's genome in the same way as described above (Goldman et al., 1990, "Transformation of *Trichoderma harzianum* by high-voltage electric pulse." Current Genetics, 17:169–174).

Finally, the third method is based on accelerating solid and dense particles that are covered with the transformant DNA; these particles are made to strike the organism to be transformed, penetrating the organism's various coverings, and once inside the organism, the DNA dissolves and integrates into its genome by mechanisms that are inherent in it (Lorito et al., 1993, "Biolistic tranformation of *Trichoderma harzianum* and *Gliocladium virent* using plasmid and genomic DNA." Current Genetics, 24:349–356

These methods are known as transformation mediated by PEG (polyethylene glycol), electroporation, and bioballistics or bombardment, respectively.

All of these methods require that the cells recover from the treatment that they receive; this is normally accomplished by placing them in culture media that contain an osmo-protector, with the transformed cells being selected later. This is done by using markers, which can be fragments of genetic information that can express themselves in the receiving organism and can complement a requirement or auxotrophy of said organism, or they confer on said organism the ability to tolerate some antibiotic, or fungicide in this case.

As a result, for a long time attempts have been made to solve the above-mentioned problems in a simple and practical way, aiming at obtaining transformed organisms with improved biological control characteristics without affecting any other of the organism's characteristics, but to date this goal has not been achieved by a simple and easily implemented method.

OBJECTS OF THE INVENTION

Considering the deficiencies of the prior arts, one object of this invention is to provide a method of obtaining strains of Trichoderma spp. that are improved in their capacity as biological control agents, whereby said method makes it to produce in an adequate manner strains of Trichoderma spp. that are more effective at biological control.

Another object of this invention is to provide a method of obtaining strains of Trichoderma spp. that are improved in their capacity as biological control agents, whereby said method makes it possible to obtain transformed organisms with improved biological control characteristics without affecting any other of the organism's characteristics.

A further object of this invention is to provide a method of obtaining strains of Trichoderma spp. that are improved in their capacity as biological control agents, whereby said method employs recombinant DNA techniques for producing transgenic organisms which over-produce the proteinase PrB1.

An additional object of this invention is to obtain a transgenic strain of *Trichoderma harzianum* IMI 206040 that has improved effectiveness as a biological control agent for phytopathogenic fungi.

BRIEF DESCRIPTION OF THE DRAWINGS

The novel aspects that are considered characteristics of this invention will be set forth in detail in the attached claims. However, in terms of both its organization and its method of operation, this invention, along with other objects and advantages of it, will be better understood from the following detailed description of certain specific embodiments when read in connection with the attached drawings, where:

DETAILED DESCRIPTION

This invention pertains to the methods that make it possible to improve strains of Trichoderma, as well as the strains obtained by this method, by modifying in a specific way one of the characteristics that are important for the biological control of phytopathogenic fungi and nematodes by integrating a specific DNA sequence into the genomes of the strains.

Figure 1:
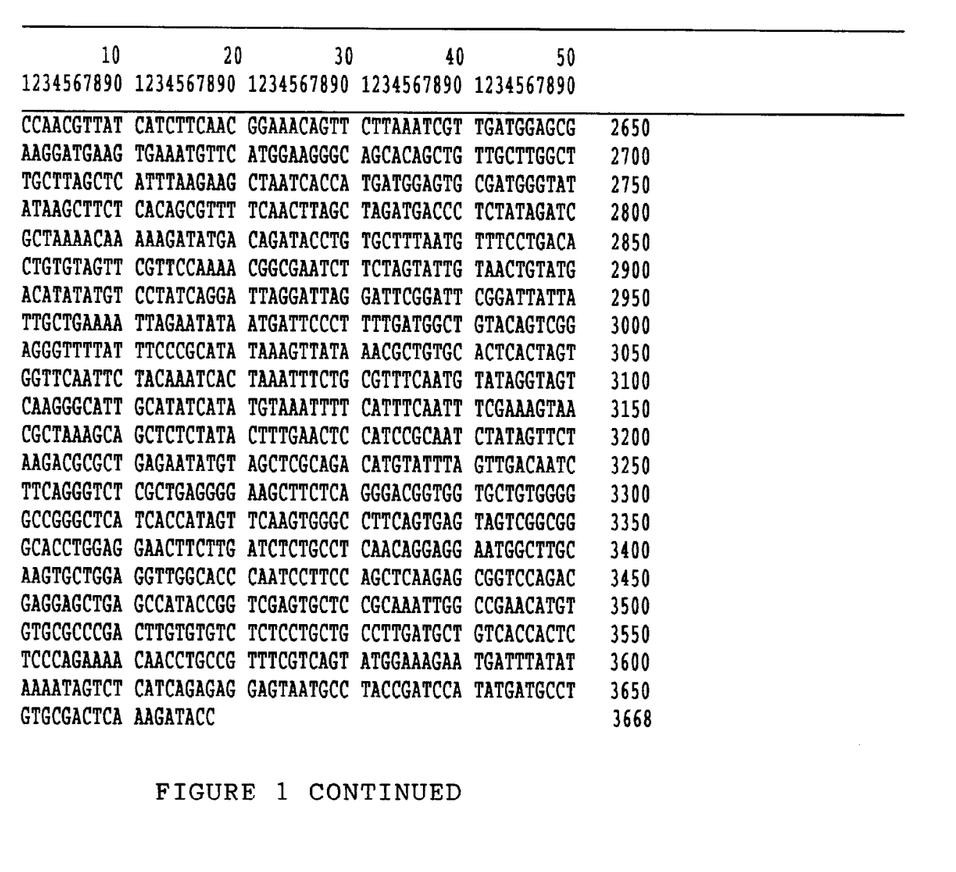
FIG. 1 shows a nucleotide sequence of the gene prb1 (SEQ ID NO:1).

The method of this invention makes it possible to obtain strains of Trichoderma that are able to achieve better biological control with the gene of interest prb1, whose nucleotide sequence is shown in FIG. 1, by introducing the gene into a DNA structure that contains functional sequences in Trichoderma which code for the proteinase PrB1 of Trichoderma.

The proteinase PrB1 will be secreted in particularly large quantities during the micoparasite process; this makes it possible to attack the cell wall of both the pathogenic fungus and the nematode.

The cell walls of the majority of fungi consist of filaments of chitin and/or β-glucanes embedded in a protein matrix, and in nematodes there is a protective protein cover; therefore the over-production of proteinase will be a very important factor in the disaggregation of said wall.

The cell wall of the phytopathogen will initially be attacked by the proteinase, and its subsequent action in combination with chitinases and β-glucanes (normally produced by Trichoderma) will lead to the destruction of the phytopathogen's cell wall and to the invasion of its cells, ultimately resulting in its death in connection with the antibiotics produced by Trichoderma.

The structure that is of interest can be introduced as a plasmid without selection, or just the sequence that is of interest, but a check is made of the transformants that over-produce proteinase using a culture medium in which it is possible to discern protein degradation halos (in this case no foreign sequence will be introduced into Trichoderma), or as part of the same plasmid that is used to select the transformants, or as two separate molecules, one with the structure of interest and with the other used to select the transformants.

The modified strains can be selected after transformation by using a DNA sequence that imparts resistance to the fungicide benomil. If this is the case, it is possible to use a DNA sequence with these characteristics; said sequence comes from the same Trichoderma and imparts resistance to the chemical thanks to a modification of the gene that codes for a β-tubulin; said modification frequently occurs naturally.

The proteinase PrB1 is coded by the genome of strains of Trichoderma spp.; said strains are characterized by their good suitability as biological control agents. The gene that codes the proteinase is contained in a DNA fragment of 5.5 kpb, which belongs to chromosome VI of the *Trichoderma harzianum* IMI 206040 strain. The mature protein that is produced from this gene is normally secreted as a polypeptide of 31 kD, with a proteolytic activity of the chemotrypsin type, which is produced "in vitro" in a specific way under simulated micoparasitism conditions or by inducing the fungus to grow in the cell walls of a pathogenic fungus.

As mentioned, the method of this invention mainly utilizes direct transformation methods with DNA that use the gene prb1.

The direct transformation methods that can be used include, among others, transformation mediated by PEG (polyethylene glycol), electroporation, and bioballistics or bombardment.

The method of PEG-mediated transformation makes use of protoplasts and is mediated by polyethylene glycol and calcium chloride.

The electroporation method can be electroporation of osmotically sensitive cells, or electroporation of intact cells.

The bioballistics or bombardment method can be bombardment with particles/bioballistics on intact spores or on a mycelium, or on osmotically sensitive cells.

In a specific embodiment of this invention, the method for obtaining strains of Trichoderma spp. that are improved in their capacity as biological control agents uses methods of direct DNA transformation that employ the gene prb1.

The method basically includes the stages as follows: transformation of Trichoderma cells with the gene of interest by co-transformation of a vector that contains the gene of interest and other accessory sequences, along with an auxiliary plasmid that carries the functions that are necessary for the selection of the transgenic strains; or transformation with a vector that contains the gene of interest and accessory sequences, in which vector the sequences that are necessary for transformant selection are in the same replicon; finally, obtaining transformed Trichoderma cells in which the gene of interest has been integrated into their genomes.

The nucleic acid sequences that are used for selection may contain a functional marker gene in Trichoderma, or inside of the nucleic acid sequences used there may be a molecule of recombinant DNA that codes for resistance to antibiotics, resistance to a herbicide, resistance to a fungicide, for complementation of an auxotrophy, or one that codes for a reporter gene.

The plasmid that is the vehicle for the sequence of interest may be a molecule that includes a plasmid which is able to replicate itself in *Escherichia coli* containing a marker for resistance to antibiotics and a molecule of recombinant DNA that includes: a promoter sequence(s) that function(s) in Trichoderma for the production one or two RNA sequences; DNA structural sequences that lead to the production of RNA sequences which code either for the proteinase PrB1 or for proteinase PrB1 and for the selection marker; and a DNA sequence(s) 3' that function(s) in Trichoderma, resulting in the termination of transcription and the addition of polyadenylated sequences at end 3' of the corresponding RNA sequence(s).

The auxiliary plasmid which carries the functions that are necessary for the selection of the transgenic strains is a molecule that includes a plasmid which is able to replicate itself in *Escherichia coli* containing a marker for resistance to antibiotics and a molecule of recombinant DNA that includes: a promoter sequence that functions in Trichoderma for the production of an RNA sequence that codes for the selection marker, and DNA structural sequences that lead to the production of RNA sequences which code the selection marker.

In an additional embodiment the plasmid that is the vehicle for the sequence of interest can be a molecule which includes a plasmid that is able to replicate itself in *Escherichia coli* containing a marker for resistance to antibiotics and a molecule of recombinant DNA that includes: a promoter sequence which comes from another organism or from the Trichoderma itself and which is not part of the prb1 gene but which functions in Trichoderma for the production of an RNA sequence, or a promoter sequence which comes from another organism or from the Trichoderma itself and which is not part of the prb1 gene but which functions in Trichoderma for the production of an RNA sequence of interest and another promoter sequence that will guide the expression of the selection marker; DNA structural sequences that lead to the production of RNA sequences which code for the proteinase PrB1 or for the proteinase PrB1 and for the selection marker; and a DNA sequence(s) 3' that function(s) in Trichoderma, leading to the termination of transcription and to the addition of polyadenylated sequences at end 3' of the corresponding RNA sequence(s).

In another preferred embodiment of this invention, the method includes the stages of: transformation of Trichoderma cells with a vector that contains the gene of interest and accessory sequences, and obtaining transformed Trichoderma cells in which the gene of interest has been integrated into their genomes.

The plasmid that is the vehicle for the sequence of interest can be a molecule which includes a plasmid that is able to replicate itself in *Escherichia coli* containing a marker for resistance to antibiotics and a molecule of recombinant DNA that includes: a promoter sequence that functions in Trichoderma for the production of an RNA sequence; DNA structural sequences that lead to the production of RNA sequences which code for the proteinase PrB1; and a DNA sequence 3' that functions in Trichoderma, leading to the termination of transcription and to the addition of polyadenylated sequences at end 3' of the corresponding RNA sequence.

An additional embodiment of the method of this invention includes the stages of: transformation of Trichoderma cells with a molecule of recombinant DNA that contains the gene of interest, and obtaining transformed Trichoderma cells in which the gene of interest has been integrated into their genomes.

The sequence of interest is a molecule which includes a molecule of recombinant DNA that contains: a promotor sequence that functions in Trichoderma for the production of an RNA sequence; DNA structural sequences that lead to the production of RNA sequences which code for the proteinase PrB1; and a DNA sequence 3' that functions in Trichoderma, leading to the termination of transcription and to the addition of polyadenylated sequences at end 3' of the corresponding RNA sequence.

The sequence of interest can also be a molecule that includes a molecule of recombinant DNA which includes: a promotor sequence which comes from another organism or from the Trichoderma itself and which is not part of the prb1 gene but which functions in Trichoderma for the production of an RNA sequence; DNA structural sequences that lead to the production of RNA sequences which code for the proteinase PrB1; and a DNA sequence 3' that functions in Trichoderma, leading to the termination of transcription and to the addition of polyadenylated sequences at end 3' of the corresponding RNA sequences.

The strain that is obtained by the method of this invention is a transgenic strain of *Trichoderma harzianum* IMI 206040 that has improved efficiency in terms of biological control of phytopathogenic fungi; said strain is produced by introducing multiple copies of the gene prb1 that are integrated into their genomes in a stable manner.

This strain is able to produce more RNA from prb1 and consequently secretes a larger amount of the proteinase PrB1, and is thus more effective at controlling nematodes.

EXAMPLE 1

Using one the possible variants of the methods described in this invention, improved strains of *Trichoderma harzianum* IMI 206040 were created in which it was confirmed that they had an improved ability to control a phytopathogenic fungus.

Figure 2:
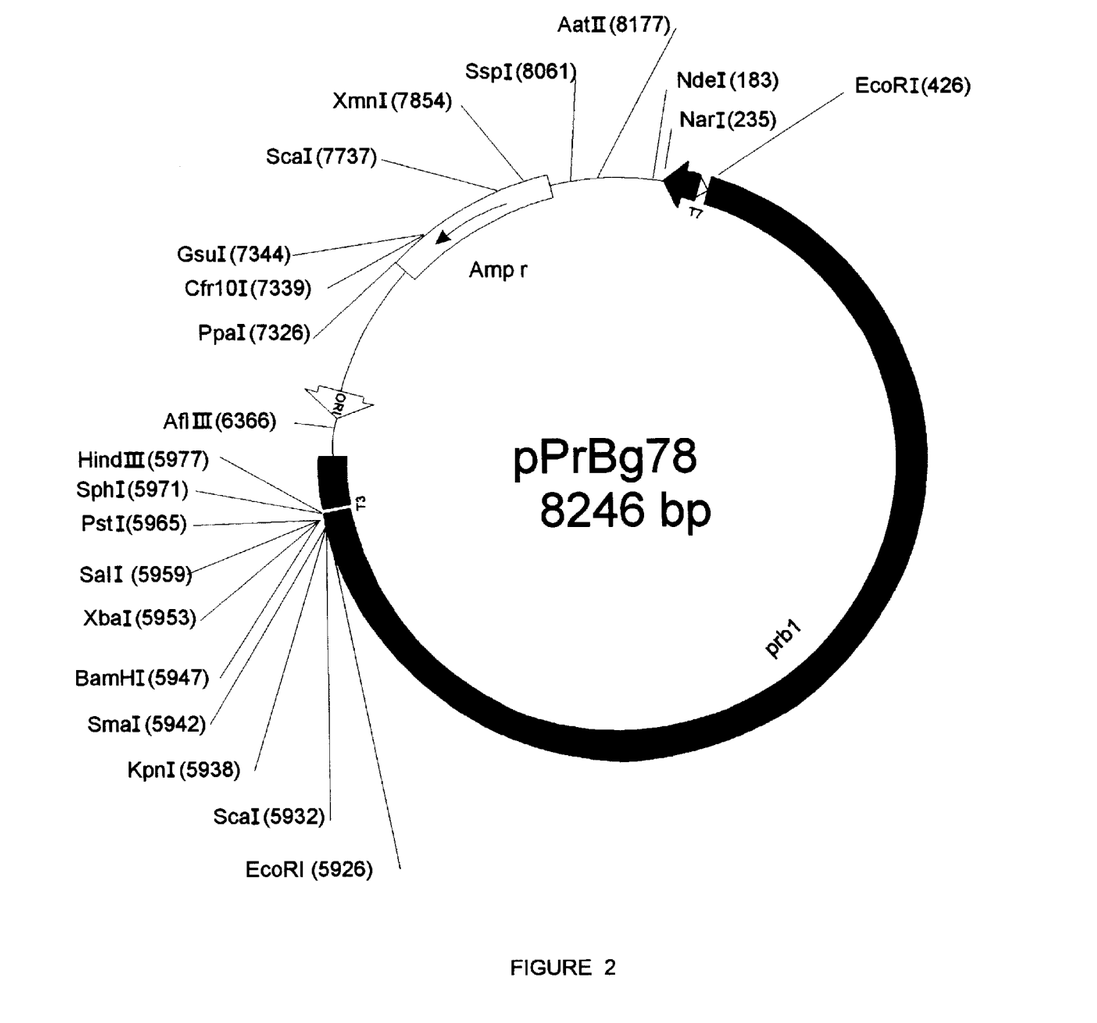
FIG. 2 is a structure of the plasmid that contains the gene prb1.
Figure 3:
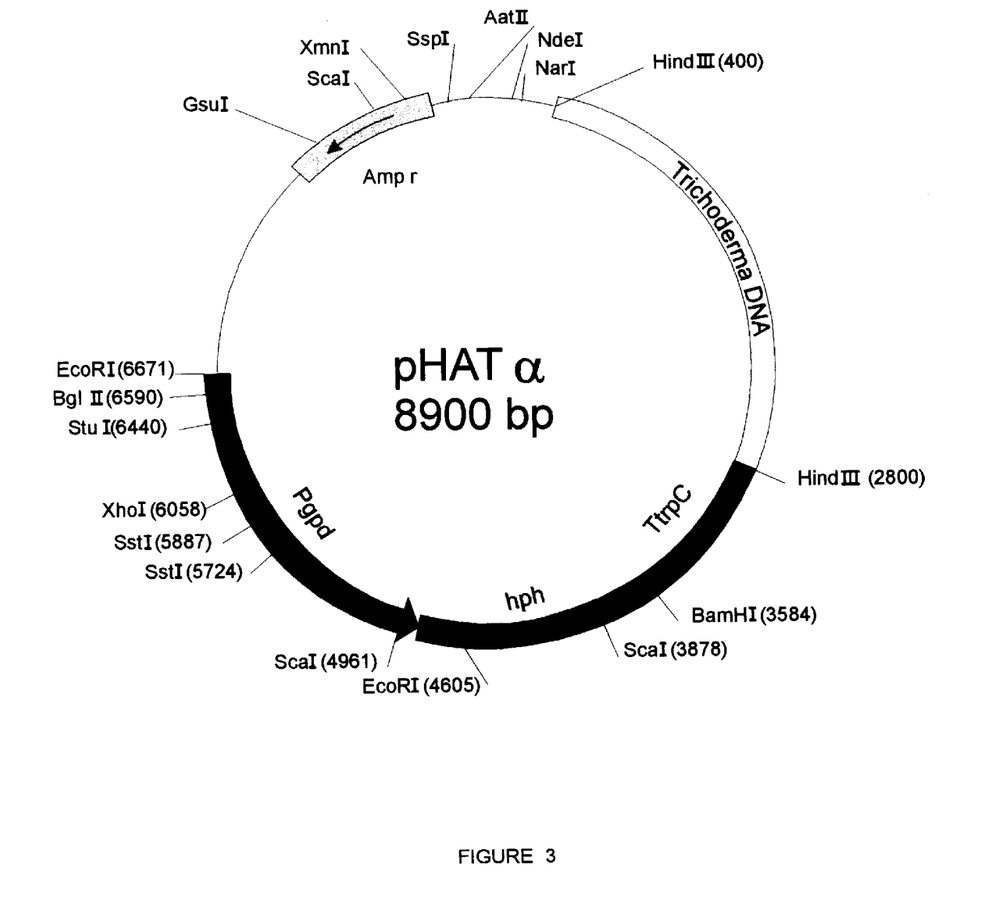
FIG. 3 shows a plasmid that contains the elements that are necessary for the selection of transformant strains in Trichoderma spp., in which hph represents the gene of *Escherichia coli* for resistance to hygromycin.
Figure 4:
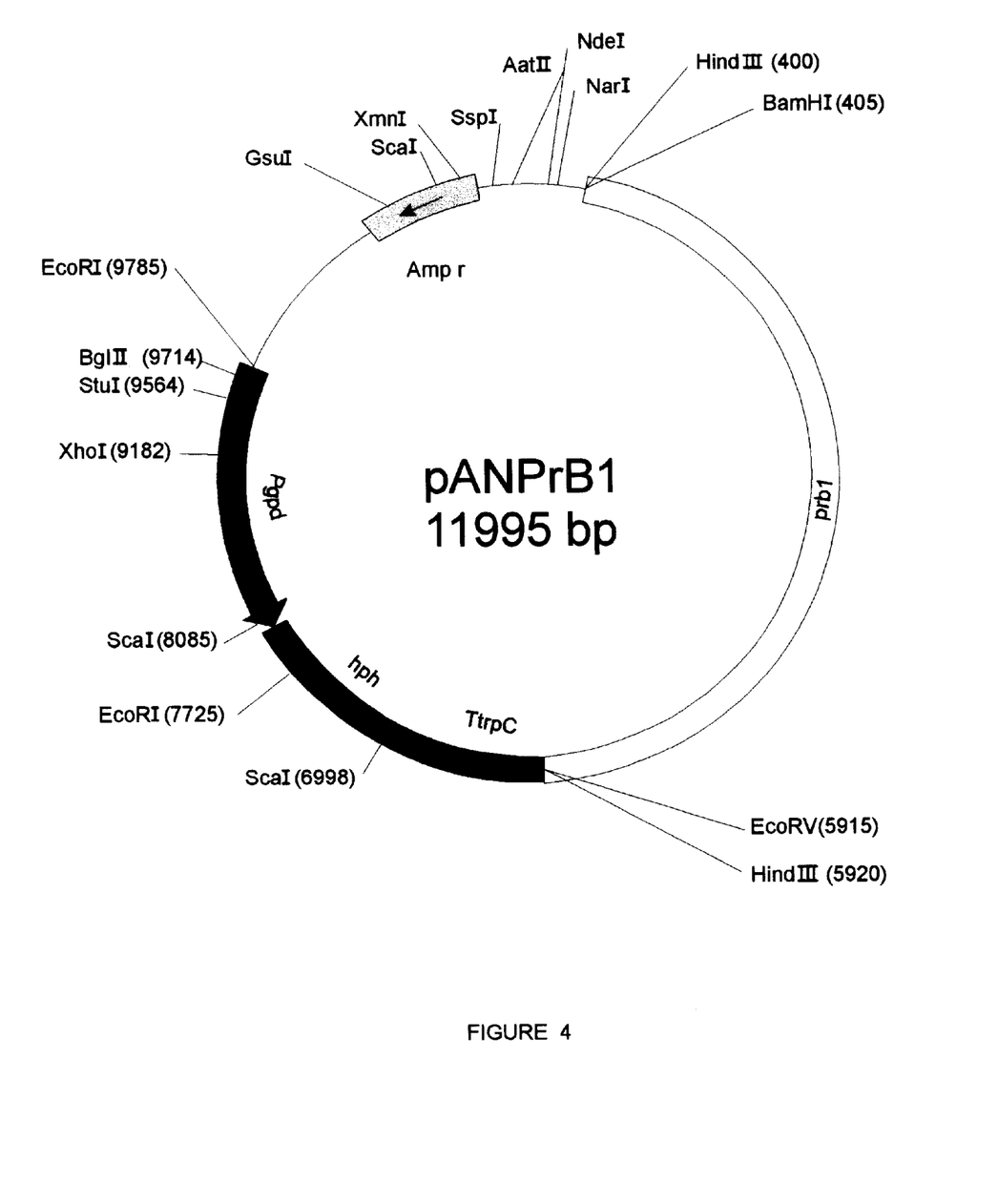
FIG. 4 shows a plasmid that contains both the gene prb1 and the elements that are necessary for the selection of transformant strains in Trichoderma, where hph represents the gene of *Escherichia coli* for resistance to hygromycin.

Stated briefly, the experiment consisted of forming protoplasts using Novozyme 234™, which were transformed by the PEG-CaCl$_2$ technique using the plasmids pPrBg78 and pHATα, as shown in FIGS. 2 and 3, where the plasmid pPrBg78 contains all of the information that is necessary for the expression of the gene prb1 in Trichoderma and pHATα contains the elements that are necessary for selecting the transgenic strains by means of their resistance to the antibiotic hygromycin B. In FIG. 3 hph represents the gene of *Escherichia coli* for resistance to hygromycin.

A series of transformants was selected that contained multiple copies of prb1 in their genomes; four of these transgenic strains and the uncultivated strain were used in greenhouse experiments, as described below.

The experiments were carried out on six replicas of young cotton plants, using plastic flowerpots with 0.5 kg of sandy loam soil (82.3% sand, 2.3% silt, 15% clay, and 0.4% organic matter; pH 7.4 and moisture retention capacity 12.2%). Ten plants were used for each replica of the experiment, and they were repeated twice.

The temperature was kept between 27 and 30° C., and irrigation was done daily.

To the soil was added *Trichoderma harzianum* with a mixture that was prepared with wheat bran/peat (0.5% weight/weight), and *Rhizoctonia solani*, prepared as chopped potato soil, was used to infest the soil.

Figure 5:
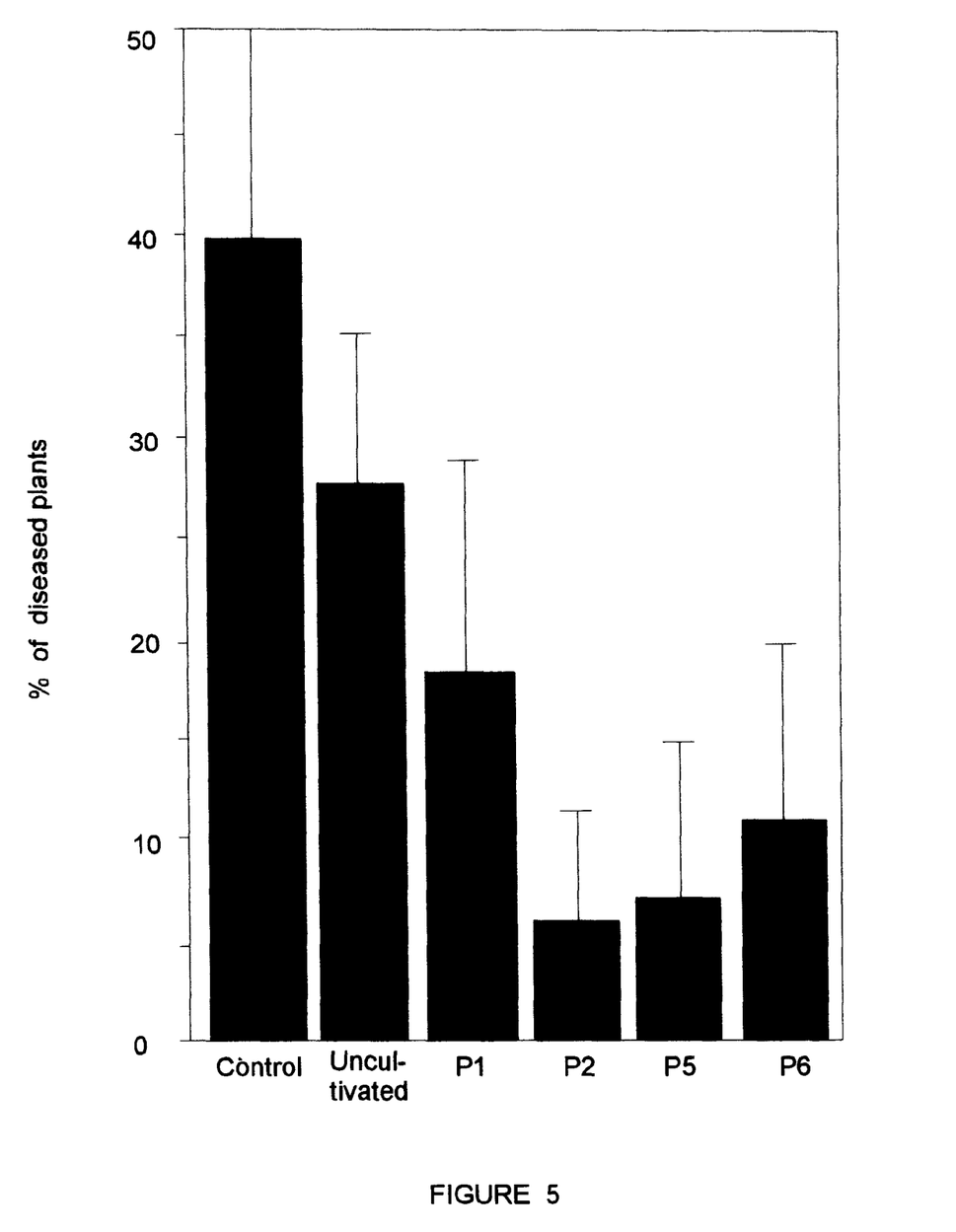
FIG. 5 shows a graph of the behavior of the modified strains in controlling *Rhizoctonia solani* in cotton plants in a greenhouse.

The results of these experiments showed that the incidence of disease caused by *Rhizoctonia solani* was 43.5% when *Trichoderma harzianum* was not used as a control agent; 27.5% when the uncultivated strain of *Trichoderma harzianum* was used; and 16.6%, 5.3%, 6.8%, and 10.5%, respectively, when the transgenic strains P1, P2, P5, and P6 were used, as FIG. 5 shows.

In FIG. 5, the bar that represents the control corresponds to plants planted in soil infested with *Rhizoctonia solani;* the uncultivated bar corresponds to soil with *Rhizoctonia solani* and to a strain of *Trichoderma harzianum* without modification; and bars P1, P2, P5, and P6 correspond to four strains that were modified by the method of this invention.

Even though certain specific embodiments of this invention have been illustrated and described, it should be emphasized that numerous modifications to said embodiments are possible. This invention should thus not be considered restricted except as required by the prior art and by the spirit of the attached claims.

*Trichoderma harzianum* IMI 206040 is a publicly available strain and may be obtained from the International Mycological Institute, Bakeham Lane, Egham, Surrey TW20 9TY, UK. Ordering information may be obtained through www.imi@cabi.org on the Internet.

We claim:

1. A method of obtaining a strain of Trichoderma species that is improved in its capacity as a biological control agent of phytopathogenic fungi, said method comprising transforming a Trichoderma species with a prb1 gene by direct transformation, wherein the prb1 gene encodes proteinase PrB1 which improves the Trichoderma species in its capacity as a biological control agent of phytopathogenic fungi.

2. The method according to claim 1, wherein said method comprises the steps of:
   a) cotransforming cells of a Trichoderma species with
      i) a first vector comprising the prb1 gene expressed from a promoter which functions in Trichoderma, and
      ii) a second vector comprising a gene encoding a selectable marker, said gene encoding a selectable marker expressed from a promoter which functions in Trichoderma,
   so as to produce transformed cells; and
   b) selecting said transformed cells of the Trichoderma species in which the selectable marker is expressed and in which the prb1 gene has been integrated into the genome of the transformed cells.

3. A method according to claim 1, wherein the method of direct transformation comprises electroporation of intact cells.

4. A method according to claim 1, wherein the method of direct transformation comprises bombarding osmotically sensitive cells with particles or bioballistics.

5. A method, according to claim 2, wherein the selectable marker comprises a functional marker gene in Trichoderma.

6. A method, according to claim 2, wherein the selectable marker comprises a recombinant DNA molecule which codes for resistance to antibiotics.

7. A method, according to claim 2, wherein the selectable marker comprises a recombinant DNA molecule which codes for resistance to a herbicide.

8. A method, according to claim 2, wherein the selectable marker comprises a recombinant DNA molecule which codes for resistance to a fungicide.

9. A method, according to claim 2, wherein the selectable marker comprises a recombinant DNA molecule which codes for complementation of an auxotrophy.

10. A method, according to claim 2, wherein the selectable marker comprises a recombinant DNA molecule which codes for a reporter gene.

11. A method, according to claim 2, wherein said first vector comprises:
    a) a plasmid which is able to replicate in *Escherichia coli* containing a marker for resistance to antibiotics; and
    b) a molecule of recombinant DNA comprising:
       i) a promoter that functions in Trichoderma for the production of an RNA sequence;
       ii) DNA structural sequences that lead to the production of RNA which encodes the proteinase PrB1; and
       iii) a DNA sequence 3' of said structural sequences that functions in Trichoderma, resulting in termination of transcription and addition of polyadenylated sequences 3' of said RNA which encodes PrB1.

12. A method, according to claim 2, wherein said second vector comprises:
    a) a plasmid which is able to replicate in *Escherichia coli* containing a selectable marker for resistance to antibiotics; and
    b) a molecule of recombinant DNA comprising:
       i) a promoter that functions in Trichoderma to produce an RNA that encodes the selectable marker; and
       ii) DNA structural sequences that lead to the production of RNA which encodes the selectable marker.

13. A method, according to claim 2, wherein said first vector comprises:
    a) a plasmid which is able to replicate in *Escherichia coil* containing a marker for resistance to antibiotics; and
    b) a molecule of recombinant DNA comprising:
       i) a promoter sequence which comes an organism other than Trichoderma or which comes from Trichoderma itself and which is not part of the Trichoderma prb1 gene but which functions in Trichoderma for the production of RNA;
       ii) DNA structural sequences that lead to the production of RNA which encodes the proteinase PrB1; and
       iii) a DNA sequence 3' of said structural sequences that functions in Trichoderma, resulting in termination of transcription and addition of polyadenylated sequences 3' of said RNA which encodes PrB1.

14. A method according to claim 1, comprising the steps of:
    a) transforming with a vector comprising:
       i) a first DNA comprising the prb1 gene, and
       ii) a second DNA comprising a selectable marker,
    wherein said first DNA and said second DNA are in the same replicon; and
    b) selecting transformed Trichoderma cells in which said prb1 gene has been integrated into the genomes of the transformed cells.

15. A method, according to claim 14, wherein said selectable marker comprises a functional marker gene in Trichoderma.

16. A method according to claim 14, wherein said selectable marker comprises a recombinant DNA molecule which codes for resistance to antibiotics.

17. A method according to claim 14, wherein said selectable marker comprises a recombinant DNA molecule which codes for resistance to a herbicide.

18. A method, according to claim 14, wherein said selectable marker comprises a recombinant DNA molecule which codes for resistance to a fungicide.

19. A method, according to claim 14, wherein said selectable marker comprises a recombinant DNA molecule which codes for complementation of an auxotrophy.

20. A method according to claim 14, wherein said selectable marker comprises a recombinant DNA molecule which codes for a reporter gene.

21. A method according to claim 14, wherein said vector comprises:
   a) a plasmid which is able to replicate in *Escherichia coli* containing a selectable marker for resistance to antibiotics; and
   b) recombinant DNA that comprises:
      i) a promoter sequence that functions in Trichoderma for the production of RNA sequences;
      ii) DNA structural sequences that lead to the production of RNA sequences which encode the proteinase PrB1 and the selectable marker; and
      iii) DNA sequences 3' of said structural sequences and 3' of said selectable marker that function in Trichoderma, resulting in termination of transcription and addition of polyadenylated sequences 3' of said RNA sequences which encode PrB1 and the selectable marker.

22. A method, according to claim 14, wherein said vector comprises:
   a) a plasmid which is able to replicate itself in *Escherichia coli* containing a selectable marker for resistance to antibiotics, and
   b) a molecule of recombinant DNA comprising:
      i) a first promoter sequence which comes from an organism other than Trichoderma or from Trichoderma itself and which is not part of the Trichoderma prb1 gene but which functions in Trichoderma for the production of a prb1 RNA sequence;
      ii) a second promoter sequence that promotes the expression of the selectable marker;
      iii) DNA structural sequences that lead to the production of RNA sequences which encode the proteinase Prb1;
      iv) DNA structural sequences that lead to the production of RNA sequences which encode the selectable marker;
      v) DNA sequences, 3' of the structural sequences encoding PrB1, that function in Trichoderma, resulting in termination of transcription and addition of polyadenylated sequences 3' of said RNA sequences encoding PrB1; and
      vi) DNA sequences, 3' of the structural sequences encoding the selectable marker, that function in Trichoderma, resulting in termination of transcription and addition of polyadenylated sequences 3' of said RNA sequences encoding said selectable marker.

23. A method according to claim 1, comprising:
   a) transforming with a vector comprising prb1 structural sequences of said prb1 gene that lead to the production of RNA sequences which encode the proteinase PrB1, a promoter for said prb1 gene, and DNA sequences 3' of said structural sequences which cause termination of transcription and addition of polyadenylated sequences 3' of said RNA sequences which encode prB1; and
   b) selecting transformed Trichoderma cells in which the prb1 gene has been integrated into the genomes of the transformed cells.

24. A method according to claim 23, wherein said vector comprises:
   a) a plasmid which is able to replicate itself in *Escherichia coli* containing a marker for resistance to antibiotics, and
   b) a molecule of recombinant DNA comprising:
      i) a promoter which functions in Trichoderma for the production of an RNA sequence;
      ii) DNA structural sequences that lead to the production of RNA which encodes the proteinase PrB1; and
      iii) a DNA sequence 3' of said structural sequences that functions in Trichoderma, resulting in termination of transcription and addition of polyadenylated sequences 3' of said RNA which encodes PrB1.

25. A method according to claim 1, comprising:
   a) transforming with a molecule of recombinant DNA comprising prb1; and
   b) selecting transformed Trichoderma cells in which the prb1 gene has been integrated into the genomes of the transformed cells.

26. A method according to claim 25, wherein said molecule of recombinant DNA comprises:
   i) a promoter that functions in Trichoderma for the production of an RNA;
   ii) DNA structural sequences that lead to the production of RNA which encodes the proteinase PrB1; and
   iii) a DNA sequence 3' of said structural sequences that functions in Trichoderma, resulting in termination of transcription and addition of polyadenylated sequences 3' of said RNA sequence which encodes PrB1.

27. A method according to claim 25, wherein the recombinant DNA comprises:
   i) a promoter which comes from another organism or from Trichoderma itself and which is not part of the Trichoderma prb1 gene but which functions in Trichoderma for the production of an RNA sequence;
   ii) DNA structural sequences that lead to the production of RNA sequences which encode the proteinase PrB1; and
   iii) a DNA sequence 3' that functions in Trichoderma, resulting in termination of transcription and addition of polyadenylated sequences 3' of the RNA encoding PrB1.

28. A transgenic strain of *Trichoderma harzianum* IMI 206040 having improved effectiveness as a means of biological control for phytopathogenic fungi as compared to naturally occurring *Trichoderma harzianum*, wherein said transgenic strain is produced by introducing multiple copies of a Trichoderma prb1 gene which become integrated into the genomes of said transgenic strain in a stable manner, wherein said transgenic strain produces more RNA encoding PrB1 than is produced in a naturally occurring strain of *Trichoderma harzianum* and said transgenic strain consequently secretes a larger amount of the proteinase PrB1 than does a naturally occurring strain of *Trichoderma harzianum*.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 3668 base pairs
        (B) TYPE: nucleic acid
        (C) STRANDEDNESS: double
        (D) TOPOLOGY: linear     (ii) MOLECULE TYPE: DNA (genomic)

(iii) HYPOTHETICAL: NO

(vi) ORIGINAL SOURCE:
        (A) ORGANISM: Trichoderma harzianum     (xi) SEQUENCE DESCRIPTION: SEQ ID NO:1:

```
AATTCAACTT TATTCACAAC GTTTTTTGTC GACTTCTAGC TTAGAGCTAC TGTATTTGTT      60

AATATTTGTT CAGTGGCTGC AAAATTACAT CCCAAGCCAT TCGCTGCTAC ATAAATCATG     120

GGCTATAAGA ACCAACACAA TTCTTATTAG ACGTAGTAAT ACCTAGGTAC CTTACTTGGC     180

AATACGCCTT ACGATGAGTT CAATGTGGGG ATTTTATGAG CAAAGATTGA AAATATTGAT     240

GCAATTACTT TTTCGGGTAT TGGTTTCCAC TTGCGGAAGA CTGTCTAGTA GTACATCTTT     300

CACGATCAAA AATATCACAT GTCGTTTACC ATCTCTTATC GCTCACAATC TTCAGCCGCC     360

TTGTAGGAGC AGCATGGATA ATAATCCGAG ATCCCAGCGC TCTATAATAG CGGATTCCCC     420

ATAACGTACA ATCCGTAATA TTGAAAACTT TGGTTACTCA GCGAGGTGGC AGAATCACCT     480

TCCCATTCGG GCAATATAAA AAGTTCCGCT ATTCGGCCAC CCCTCCTTCT TAAATCTTGA     540

TAAGGCGCCG GCTATGATTG CGCTATTAGA GCCTTGCCGT GCGTTCTATT CAAAGGTTCC     600

TTGATTCTCG GACATGATAA CTTAAAAAGC AGGTGCACAG CTATTGGCGC GATTTTAGTC     660

CGCACGGCAT TCGGCATTTT TACCTGTGAT ACAAACAACC CATCGAGAGT TCGATTTTAA     720

GCGTAAATAT TAGCGAATCT TAGTCTATAG GCGTCAAATA ACCTTAAATG AATCTTAAAT     780

TGTATGGGTT CGCTATTTGT ATTATTTGTC CGGTAGTGAT GAGGAGATTG GAGACAGCGC     840

ATTTGGAGTG GGAATGATGA AAAGCAAGAC GGCTATTCAT AGAAATAGAC CATGTATTAA     900

ACCATCTTCA TCGATATCCA AGTTGATGCC TTGGAGATAC TGCTTCTTCA TCATGCTTCT     960

TTCCGCATTC AAACTAGCTG CCAAGATCTG GGCACCGTGG CTGCCGTAAC ACAAACCTAT    1020
```

-continued

| | | | | | |
|---|---|---|---|---|---|
|AGTCTTGGTG|TGATCTATTC|GTTCTAGTTC|TTTTTAGGCA|GCTTGGATAT|CTATACTCAG 1080|
|CGGCTTGGCA|AGCAATTACA|ATGGAGTGAT|TCTGGCAGAC|GTGATGGAGG|CTTCAGATAG 1140|
|CGAAATCGAG|CATATCATCC|GCAGTGACAA|TGAAAACTAT|TTAAGTTGGC|TGTATTCGCA 1200|
|AGAATATCTG|GTAAGTTGGA|ACAGCCATCG|ACTTCCTATC|TTTTCTCCTC|CACTATACAA 1260|
|AGCACATCAC|AGCCATGACC|AGCATTCGTC|GTCTCGCTCT|CTATCTTGGA|GCTTTGCTCC 1320|
|CGGCTGTCCT|CGCTGCTCCT|GCAGCTCTTC|ACAAGAAGCC|TGAAGCCGTA|CCCAACAAGT 1380|
|TCATCGTCAC|TCTTAAAGAG|GGTGCTTCTA|TTGATACCGA|CTCTCATCTC|GCCTGGGTAA 1440|
|CGGACATCCA|CACCCGTTCG|TTGACCAAGC|GTAGCACTGC|TGGTGTTGAA|AAGACTTATA 1500|
|ACATTCATAC|TTGGAATGCT|TATGCGGGCG|AGTTTGACGA|GGAGACAATT|GAGCAGATCA 1560|
|AGTCCAACCC|CGATGTACGT|GTCCGCTGTA|TTGTGAAGAT|AAAAGAACAA|AAAGAAGCTA 1620|
|ATCACACTAT|AGGTTGCGTC|TGTTGAGCCA|GACTACATCA|TGCATCTGTC|GGACATTGTT 1680|
|GAAGACAAGC|GTGCTCTGAC|CACACAATCT|GGTGCTCCTT|GGGGTCTCGG|CACTGTGTCC 1740|
|CATCGCACAT|CTGGATCCAC|AAGCTACATT|TATGATAGCT|CAGCCGGCGC|CGGCACCTTT 1800|
|GCCTATGTGG|TTGACTCTGG|TATCAACACT|TCTCATCAGC|AATTCGGCGG|GCGTGCCAGC 1860|
|CTTGGCTACA|ATGCTGCAGG|AGGACAGCAT|GTCGATACTC|TTGGCCATGG|TACTCATGTT 1920|
|TCCGGAACAA|TTGGTGGATC|TACATACGGT|GTTGCTAAGC|AGGTGAGCTA|CCCTTTGTCG 1980|
|ACTTTTTGTT|GTGAATACAT|GAATGCATTC|AAGACTAACT|CGGTACTGCT|CATAGGCGAG 2040|
|CCTAATCTCT|GTCAAGGTCT|TGCTGGTGA|AAGTGCTTCC|ACCTCTGTTA|TCCTTGACGG 2100|
|CTATAACTGG|GCTCTAAACG|ACATCGTCTC|GAAAAGCCGT|GCTAGCAAGT|CTGCTATTAA 2160|
|CATGTCGCTT|GGAGGACCTG|CCTCATCTAC|CTGGACGACC|GCCATTAACG|CAGCCTTTAA 2220|
|CCAGGGCGTG|CTTACCATTG|TCGCCGCTGG|TAATGGCGAC|TCTCTGGGAA|ACCCCCAGCC 2280|
|AGTCTCCGGC|ACTTCTCCTG|CTAACGTTCC|TAACGCCATA|ACCGTTGCCG|CATTGGACAT 2340|
|CAACTGGCGC|ACTGCTTCCT|TCACCAACTA|TGGTGCTGGC|GTTGATGTTT|TTGCCCCTGG 2400|
|CGTCAACATT|CTGTCGTCAT|GGATTGGATC|CAACACTGCT|ACCAACACAA|TCAGCGGTAC 2460|
|TTCCATGGCT|ACACCTCACG|TTGTTGGCCT|GGCCCTCTAT|CTTCAATCTC|TCGAGGGTCT 2520|
|CACCTCTCCG|ACCGCTGTCA|CTAACCGAAT|TAAAGCTCTG|GCTACATCTG|GTCGTGTAAC 2580|
|CGGAAGCCTC|AACGGCAGCC|CCAACGTTAT|CATCTTCAAC|GGAAACAGTT|CTTAAATCGT 2640|
|TGATGGAGCG|AAGGATGAAG|TGAAATGTTC|ATGGAAGGGC|AGCACAGCTG|TTGCTTGGCT 2700|
|TGCTTAGCTC|ATTTAAGAAG|CTAATCACCA|TGATGGAGTG|CGATGGGTAT|ATAAGCTTCT 2760|
|CACAGCGTTT|TCAACTTAGC|TAGATGACCC|TCTATAGATC|GCTAAAACAA|AAAGATATGA 2820|
|CAGATACCTG|TGCTTTAATG|TTTCCTGACA|CTGTGTAGTT|CGTTCCAAAA|CGGCGAATCT 2880|
|TGTAGTATTG|TAACTGTATG|ACATATATGT|CCTATCAGGA|TTAGGATTAG|GATTCGGATT 2940|
|CGGATTATTA|TTGCTGAAAA|TTAGAATATA|ATGATTCCCT|TTTGATGGCT|GTACAGTCGG 3000|
|AGGGTTTTAT|TTCCCGCATA|TAAAGTTATA|AACGCTGTGC|ACTCACTAGT|GGTTCAATTC 3060|
|TACAAATCAC|TAAATTTCTG|CGTTTCAATG|TATAGGTAGT|CAAGGGCATT|GCATATCATA 3120|
|TGTAAATTTT|CATTTCAATT|TCGAAAGTAA|CGCTAAAGCA|GCTCTCTATA|CTTTGAACTC 3180|
|CATCCGCAAT|CTATAGTTCT|AAGACGCGCT|GAGAATATGT|AGCTCGCAGA|CATGTATTTA 3240|
|GTTGACAATC|TTCAGGGTCT|CGCTGAGGGG|AAGCTTCTCA|GGGACGGTGG|TGCTGTGGGG 3300|
|GCCGGGCTCA|TCACCATAGT|TCAAGTGGGC|CTTCAGTGAG|TAGTCGGCGG|GCACCTGGAG 3360|
|GAACTTCTTG|ATCTCTGCCT|CAACAGGAGG|AATGGCTTGC|AAGTGCTGGA|GGTTGGCACC 3420|

```
CAATCCTTCC AGCTCAAGAG CGGTCCAGAC GAGGAGCTGA GCCATACCGG TCGAGTGCTC    3480

CGCAAATTGG CCGAACATGT GTGCGCCCGA CTTGTGTGTC TCTCCTGCTG CCTTGATGCT    3540

GTCACCACTC TCCCAGAAAA CAACCTGCCG TTTTGTCAGT ATGGAAAGAA TGATTTATAT    3600

AAAATAGTCT CATCAGAGAG GAGTAATGCC TACCGATCCA TATGATGCCT GTGCGACTCA    3660

AAGATACC                                                            3668
```